US012728283B2

(12) United States Patent
Janson et al.

(10) Patent No.: US 12,728,283 B2
(45) Date of Patent: Sep. 8, 2026

(54) TREATMENT PLANNING USING MULTIPLE RELATIVE BIOLOGICAL EFFECTIVENESS (RBE) MODELS

(71) Applicant: RaySearch Laboratories AB (Publ), Stockholm (SE)

(72) Inventors: Martin Janson, Enskededalen (SE); Albin Fredriksson, Stockholm (SE); Erik Traneus, Uppsala (SE); Kjell Eriksson, Balsta (SE)

(73) Assignee: Raysearch Laboratories AB (publ), Stockholm (SE)

( * ) Notice: Subject to any disclaimer, the term of this patent is extended or adjusted under 35 U.S.C. 154(b) by 990 days.

(21) Appl. No.: 17/996,620

(22) PCT Filed: Apr. 9, 2021

(86) PCT No.: PCT/EP2021/059326
§ 371 (c)(1),
(2) Date: Oct. 20, 2022

(87) PCT Pub. No.: WO2021/213818
PCT Pub. Date: Oct. 28, 2021

(65) Prior Publication Data

US 2023/0211177 A1 Jul. 6, 2023

(30) Foreign Application Priority Data

Apr. 22, 2020 (EP) .................................... 20170924

(51) Int. Cl.
*A61N 5/10* (2006.01)
*G16H 20/40* (2018.01)

(52) U.S. Cl.
CPC .......... *A61N 5/1031* (2013.01); *G16H 20/40* (2018.01); *A61N 2005/1087* (2013.01)

(58) Field of Classification Search
CPC .. A61N 5/1031; A61N 5/10; A61N 2005/105; A61N 2005/1087
See application file for complete search history.

(56) References Cited

U.S. PATENT DOCUMENTS

2002/0080915 A1* 6/2002 Frohlich ................ A61N 5/103 378/65
2015/0073200 A1* 3/2015 Keppel ................ A61N 5/1031 600/1

FOREIGN PATENT DOCUMENTS

EP 1818078 A1 8/2007
JP 2009525797 A 7/2009
JP 2009531138 A 9/2009

OTHER PUBLICATIONS

Sanchez-Parcerisa et al, "MultiRBE: Treatment Planning for Protons with Selective Radiobiological Effectiveness", Medical Physics, vol. 46, No. 9, Jul. 31, 2019, p. 4276-4284 (Year: 2019).*

(Continued)

*Primary Examiner* — David E Smith
(74) *Attorney, Agent, or Firm* — Noréns Patentbyrå AB

(57) ABSTRACT

An inverse-planning method (100), by which a treatment plan specifying a non-photon irradiation of a patient including a target volume is generated, comprises: obtaining (110, 112) first and second plan goals in terms of a respective first and second numerical condition on the treatment plan's photon-equivalent dose as computed using a first and second RBE factor; and generating (114) the treatment plan by an optimization process aiming to satisfy the first, second and any further plan goals, wherein (a) the first and second plan goals apply to volumes which either are included in the TV or are completely or partially separate from the TV and/or (b) the first and second RBE factors are variable. In a further aspect, a data carrier provides a treatment plan with these (Continued)

characteristics together with reporting quantities relating to fulfilment of the first and second plan goals.

14 Claims, 2 Drawing Sheets

(56) References Cited

OTHER PUBLICATIONS

Sanches-Parcerisa et al; "MultiRBE: Treatment Planning for Protons with Selective Radiobiological Effectiveness", Medical Physics, vol. 46, No. 9, 2019 (Year: 2019).*

Wedenberg, M. et al., "A model for the relative biological effectiveness of protons: The tissue specific parameter $\alpha/\beta$ of photons is a predictor for the sensitivity to LET changes", Acta Oncologica (2013), vol. 52, pp. 580-588 [doi:10.3109/0284186X.2012.705892]).

Carabe-Fernandez, Alejandro et al., "The incorporation of the concept of minimum RBE (RBEmin) into the linear-quadratic model and the potential for improved radiobiological analysis of high-LET treatments", Int. J. Radiat. Biol. (2007), vol. 83, pp. 27-39 [doi:10.1080/09553000601087176]).

Chen, Yong et al., "Empirical model estimation of relative biological effectiveness for proton beam therapy", Radiat. Prot. Dosim. (2012), vol. 149, pp. 116-123 [doi:10.1093/rpd/ncr218]).

Hawkins, Roland B., A Microdosimetric-Kinetic Model for the Effect of Non-Poisson Distribution of LethalLesions on the Variation of RBE with LET, Radiation Research , Jul. 2003, vol. 160, No. 1 (Jul. 2003), pp. 61-69.

Kraft, G., Tumortherapy with ion beams, NIMPR 2000.

McNamara, Aimee L, et al., "A phenomenological relative biological effectiveness (RBE) model for proton therapy based on all published in vitro cell survival data", Phys. Med. Biol. (2015), vol. 60, pp. 8399-8416 [doi:10.1088/0031-9155/60/21/8399]).

Sanchez-Parcerisa, Daniel et al., MultiRBE: Treatment planning for protons with selective radiobiological effectiveness, Medical Physics_ 2019.

Scholz, M., et al., ., "Computation of cell survival in heavy ion beams for therapy. The model and its approximation", Radiat. Environ. Biophys. (1997), vol. 36, pp. 59-66 [doi:10.1007/s004110050055]).

Tseung, H. Wan Chan et al., "Clinically applicable Monte Carlo-based biological dose optimization for the treat¬ment of head and neck cancers with spot-scanning proton therapy", Int. J. Radiat. Oncol. Biol. Phys. (2016), vol. 95, pp. 1535-1543 [doi:10.1016/j.ijrobp.2016.03.041].

International Search Report & Written Opinion, European Patent Office, Jun. 2, 2021, Rijswijk, Netherlands.

Office action from Japan Patent Office dated Mar. 7, 2023 in corresponding Japanese patent application.

Office action dated Nov. 3, 2025 in corresponding Indian application No. 202217044458, Indian Patent Office, New Delhi, India.

* cited by examiner

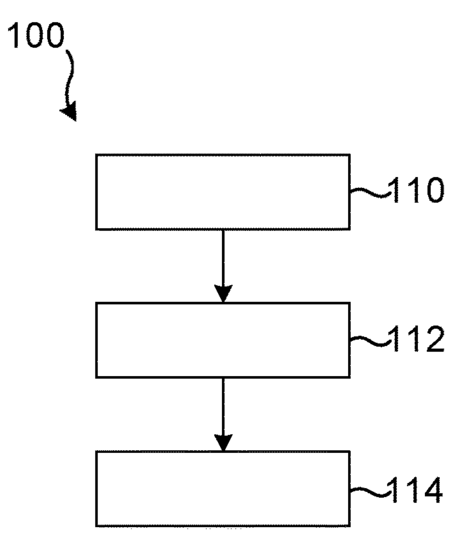
Fig. 1
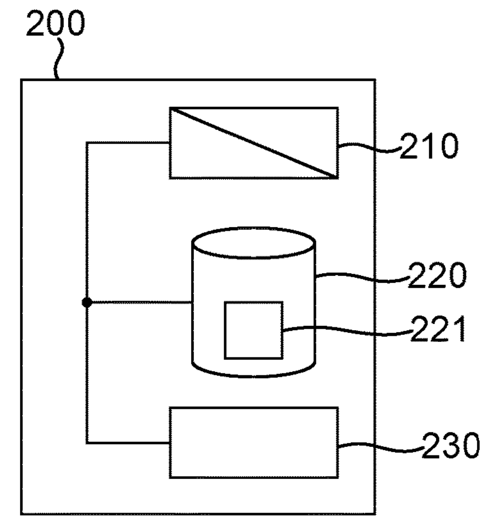
Fig. 2
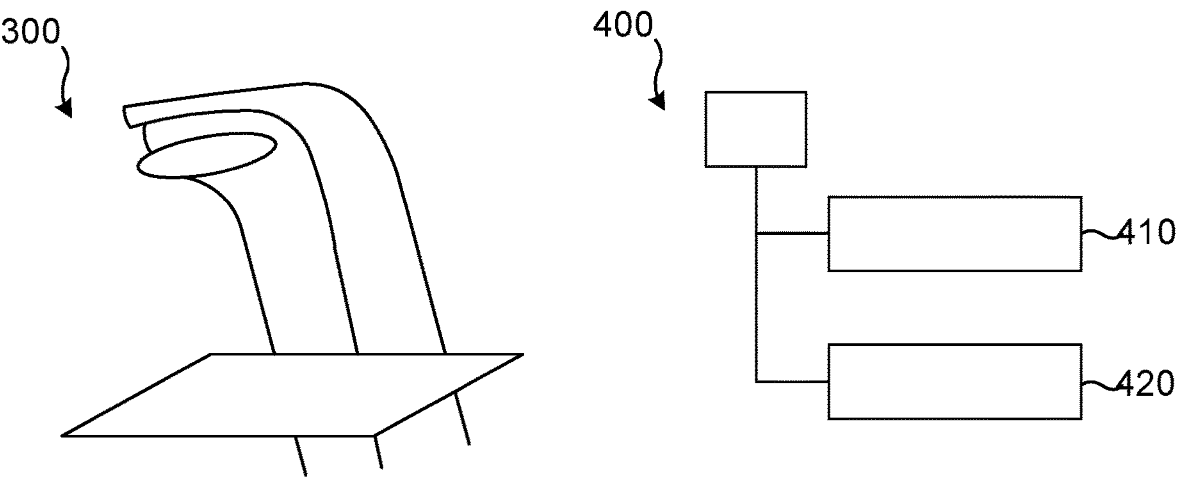
Fig. 3
Fig. 4

TREATMENT PLANNING USING MULTIPLE RELATIVE BIOLOGICAL EFFECTIVENESS (RBE) MODELS

TECHNICAL FIELD

The present disclosure relates to the field of radiation therapy and in particular to methods and devices for generating a non-photon radiation treatment plan on the basis of plan goals using two or more different relative biological effectiveness models. The disclosure further provides a data structure for sharing or storing a treatment plan with these characteristics.

BACKGROUND

Non-photon radiotherapy may utilize proton or ion radiation, in particular carbon ion radiation. According to common practice within this subfield of radiotherapy, prescriptions, clinical goals and treatment planning protocols may include specifications in terms of the photon-equivalent dose (or photon dose equivalent). The photon-equivalent dose is computed from the physical absorbed dose using the relative biological effectiveness (RBE) of the radiation used, defined as the ratio of the doses required to cause the same level of effect. The term RBE factor is used to signify the conversion factor between physical dose and photon-equivalent dose:

photon-equivalent dose=RBE factor×physical dose.

An RBE may be connected with a specific radiobiological model, which has been derived from physical and physiological considerations and possibly validated or refined experimentally. Depending on the underlying radiobiological model, the RBE factor may vary, for example, with respect to the magnitude of the physical dose or with respect to the location of the irradiated tissue. An RBE factor that depends on the physical dose will establish a non-linear relationship between physical dose and photon-equivalent dose. For example, an RBE factor proportional to the $p^{th}$ power of the physical dose, for some real $p \geq 0$, will cause the photon-equivalent dose to depend on the $(p+1)^{th}$ power of the physical dose. For proton treatment, a widely used RBE factor is the so-called 1.1 model, according to which the biological effectiveness of protons exceeds the effectiveness of photons by 10 percent regardless of the dose and other factors. It is known that the 1.1 model underestimates the dose at the distal end of a proton field. This and other effects may be taken care of by more elaborate RBE models, including those by the authors Carabe, Chen & Ahmad, McNamara and Wedenberg.

Emerging new RBE models and improvements to existing models gradually gain acceptance in the community. Clinicians may however be most familiar with the earlier models and have access to large historical data sets for these. To reap the benefits of the recent research while maintaining an ability to validate treatment plans in view of the accumulated past knowledge, it is an attractive option to process plan goals specified in terms of two or more RBE models.

The research paper Sánchez-Parcerisa et al., "MultiRBE: Treatment planning for protons with selective radiobiological effectiveness", *Med. Phys.* (2019), vol. 46, pp. 4276-4284 [doi: 10.1002/mp.13718] reports on MultiRBE, a mixed RBE model where a uniform RBE factor is used in the target volume, to ensure tumor coverage in terms of physical dose, and a variable RBE is used elsewhere.

A similar proposal, with partially different limitations, is presented in Tseung et al., "Clinically applicable Monte Carlo-based biological dose optimization for the treatment of head and neck cancers with spot-scanning proton therapy", *Int. J. Radiat. Oncol. Biol. Phys.* (2016), vol. 95, pp. 1535-1543 [doi: 10.1016/j.ijrobp.2016.03.041], which is directed to Monte Carlo-based inverse biological planning for the treatment of head and neck tumors in spot-scanning proton therapy. To create the treatment plans, the authors define constraints to maintain the physical dose within 1.25 times of the prescription dose while they maximize the target biological dose.

A still further proposal is found in US2015073200, which discloses a hadron treatment planning system which foresees a variation of the biological effect incurred by a proton beam depending on tissue depth and models the variability by applying different RBE values in different regions. A uniform relation between biological dose $D_{BIO}$ and physical dose $D_{Physical}$ is assumed, and it is used for the definition of the objective functions relating to both the organs-at-risk and the target volume.

SUMMARY

One objective of the present invention is to propose improved methods and devices for generating a non-photon radiation treatment plan on the basis of plan goals in terms of two or more different RBE models. It is a further objective to improve the transferability and storage of treatment plans with these characteristics. These and other objectives are addressed by the invention as defined by the independent claims.

In a first aspect, the invention provides an inverse-planning method for generating a treatment plan specifying a non-photon irradiation of a patient in whom a target volume (TV) is identified. The method comprises: obtaining a first plan goal in terms of a first numerical condition on the treatment plan's photon-equivalent dose as computed using a first RBE factor; obtaining a second plan goal in terms of a second numerical condition on the treatment plan's photon-equivalent dose as computed using a second, different RBE factor; and generating the treatment plan by an optimization process aiming to satisfy the first, second and any further plan goals. According to one embodiment, it is provided that (a) the first and second plan goals apply to volumes V1, V2 which either are included in the TV or are completely or partially separate from the TV, or that (b) the first and second RBE factors are variable, or that both a and b hold.

In embodiments, the further plan goals may include a third numerical condition on the treatment plan's photon-equivalent dose as computed using a third RBE factor.

As used herein, a "volume" refers to a three-dimensional region. One example is the TV, which broadly corresponds to the space occupied by a tumor in a patient's body. Particular definitions of TV include gross tumor volume, clinical target volume and planning target volume. Another example is the organ-at-risk (OAR) volume, which represents to a region where vulnerable tissue is present and dose should be controlled. A related notion is the planning organ-at-risk volume. In patents with multiple tumors or multiple organs at risk to be protected, TV and/or OAR need not be connected but may be defined as unions of mutually disjoint sub-regions. Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

By way of example, at least the following configurations are possible under option a.

a1: $V1 \subset TV$, $V2 \subset TV$, with $V1=V2$ a2: $V1=V2=TV$ a3: $V1 \subset TV$, $V2 \subset TV$, with $V1 \neq V2$ a4: $V1 \cap TV=\emptyset$, $V2 \cap TV=\emptyset$, with $V1=V2$ a5: $V1 \subset OAR$, $V2 \subset OAR$, with $V1=V2$, $V1 \subset TV$ and $V1 \cap TV \neq \emptyset$ a6: $V1 \subset OAR$, $V2 \subset OAR$, with $V1 \neq V2$, $V1 \subset TV$, $V2 \subset TV$ and $V1 \cap TV \neq \emptyset$ and/or $V2 \cap TV \neq \emptyset$ a7: $V1=V2=OAR$ a8: $V1 \cap TV=\emptyset$, $V2 \cap TV=\emptyset$, with $V1 \neq V2$.

Sub-options a1, a2 and a3 correspond to volumes included in the TV, while sub-options a4 and a8 correspond to volumes completely separate from (i.e., outside) the TV. As noted just above, OAR may be a union of mutually disjoint sub-regions. Normally the OAR is partially separate from the TV (i.e., overlapping the TV without coinciding with it) or completely separate from the TV. Under sub-options a5 and a6, at least one plan goal volume is partially separate from the TV. If the OAR is partially separate from the TV, then clearly the plan goal volume according to sub-option a7 is too. Here, the case $V1 \neq V2$ may correspond to $V1 \cap V2 \neq \emptyset$, including the special cases $V1 \subset V2$ and $V2 \subset V1$, or $V1 \cap V2=\emptyset$.

Accordingly, the first and second plan goals may relate to overlapping volumes or to coinciding volumes. This makes it possible to combine the advantages of two RBE factors for the same volume. For instance, the treatment planner may use one plan goal for the target volume with a constant RBE factor to avoid underdosage and another plan goal—still for the target volume—with a variable RBE factor to make the planning more biologically precise.

Option b, for its part, requires that neither the first nor the second RBE factor is a constant for the particular type of non-photon radiation to be delivered under the treatment plan. For example, RBE=1.1 for protons under the 1.1 model cannot constitute any of the first and second RBE factors. Indeed, while the 1.1 model certainly does not suggest that its RBE factor applies unaltered to radiation other than protons, it stipulates 1.1 as an absolute constant for protons and is therefore excluded under option b. According to this disclosure, option b instead requires that the first RBE factor shall be variable with respect to physical dose, location, particle energy or another physical, chemical or biological factor. The same requirement applies for the second RBE factor. However, option b does not exclude the case where a constant RBE factor is included in the formulation of a third plan goal which the treatment plan is to satisfy, but it suffices that two plan goals are formulated with reference to variable RBE factors.

This aspect of the invention allows a treatment plan to be generated in view of plan goals formulated in terms of multiple RBE factors. Two or more of these plan goals may relate to volumes located inside the TV or, alternatively, to volumes completely or partially separate from the TV. It is furthermore possible to combine sophisticated models involving variable RBE factors. This grants clinicians more freedom in treatment planning and may increase the precision of the radiotherapy to be delivered.

In one embodiment of the invention, the plan goals are provided to the optimization process as optimization functions. As used herein, an "optimization function" may be an objective function to be optimized (e.g. minimized), denoted $f(x)$, or a component incorporated in an objective function, denoted $f_i(x)$, where i is the index of the component. The variable x, which is typically vector-valued, represents properties of the treatment plan to be generated. The term "optimization function" also covers an expression $g_j(x)$ or $h_k(x)$ which is used to formulate a constraint $g_j(x) \leq 0$ (inequality constraint) or $h_k(x)=0$ (equality constraint), where j and k are the indices of the respective expressions, under which the optimization is performed.

In one embodiment, the plan goals are provided to the optimization process as optimization functions of the same type. Accordingly, both the first and second plan goals are incorporated in the objective function, or both the first and second plan goals are provided as constraints. Preferably, this embodiment is combined with above option a. This embodiment may render the optimization problem to be solved by the optimization process more tractable, so that an accurate solution can be achieved in shorter processing time. In other embodiments, the plan goals may be provided to the optimization process as optimization functions of different types, i.e., one incorporated in the objective function and one as a constraint.

In one embodiment, the first and second plan goals are incorporated in the objective functions as components $f_1(x)$, $f_2(x)$ of the objective function $f(x)$. In mathematical notation, the objective function may be expressed as a composition $f(x)=f(f_1(x), f_2(x))$. The composition may for example be a weighted sum $f(x)=\alpha_1 f_1(x)+\alpha_2 f_2(x)$, with nonzero coefficients $\alpha_1$, $\alpha_2$ that are equal or different. In other examples, the weighted sum may be formed after pre-composing a component $f_i(x)$ by an absolute value $|f_i(x)|$, positive part $(f_i(x))^+$, negative part $(f_i(x))^-$, power function $(f_i(x))^p$, logarithm $\ln f_i(x)$, an error function erf $f_i(x)$, an indicator function, a step function, sign function, a rounding function, another elementary or special function, or a combination of these. It is also possible to convolve a component with a mollifier function. This way, the influence of each component of the objective function can be fine-tuned and tempered relative to other components. By the use of step-like functions, undesired boundary effects or asymptotic behaviors can be eliminated. Further, the regularity of the objective function—and thereby its suitability for numerical optimization—can be improved.

The first and second plan goals may correspond to different biological endpoints or a common biological endpoint. In the present disclosure, example biological endpoints (or clinical endpoints) include disease-free survival, progression-free survival and absence of side effects in OAR. In one embodiment, the first and second plan goals correspond to different biological endpoints.

In one embodiment, each plan goal stipulates a numerical condition on the photon-equivalent dose which is a setpoint value, a lower bound, an upper bound or an interval. It is recalled that the photon-equivalent dose is understood as a value computed using the first or second RBE factor.

In a second aspect, the invention provides a treatment planning system implementing the above method. In particular, the treatment planning system may comprise an interface configured to receive the first and second plan goals. The invention furthermore provides a computer program with instructions for causing a computer, or said treatment planning system, to carry out the above method. The computer program may be stored or distributed on a data carrier.

As used herein, a "data carrier" may be a transitory data carrier, such as modulated electromagnetic or optical waves, or a non-transitory data carrier. Non-transitory data carriers include volatile and non-volatile memories, such as permanent and non-permanent storages of magnetic, optical or solid-state type. Still within the scope of "data carrier", such memories may be fixedly mounted or portable.

In a third aspect, the invention provides a data structure comprising a treatment plan component and a reporting component. The treatment plan component may contain instructions which will cause a radiation delivery system to carry out a treatment plan specifying a non-photon irradiation of a patient including a TV. The reporting component may contain two or more reporting quantities. A first reporting quantity relates to a first plan goal in terms of a first numerical condition on the treatment plan's photon-equivalent dose as computed using a first RBE factor. A second reporting quantity relates to a second plan goal in terms of a second numerical condition on the treatment plan's photon-equivalent dose as computed using a second, different RBE factor. Regarding the plan goals, above-described option a and/or option b applies.

The data structure according to the third aspect of the invention allows sharing and storage of a treatment plan generated on the basis of plan goals using two or more different relative biological effectiveness models. Not only does the data structure provide instructions for operating a radiation delivery system (treatment plan component) but it also contains reporting quantities allowing a recipient to verify that both plan goals have been met to a satisfactory extent (reporting component). For example, the recipient may be a clinician or prescription issuer, who has assigned the treatment planning task to an external party; before such an externally prepared treatment plan is executed, it is desirable to inspect the photon-equivalent dose, from the viewpoint of each RBE model, which the patient will receive. While the clinician may have instructed the external party- or the prescription may have been expressed—in terms of the photon-equivalent dose under two different RBE models, this is no essential feature of the third aspect of the invention.

In one embodiment, the reporting quantity for one plan goal is a distribution of said photon-equivalent dose (under the RBE model concerned) for a plurality of spatial points or voxels, a dose-volume histogram for said photon-equivalent dose (under the RBE model concerned), a minimum, maximum, average, median, variance, standard deviation or coefficient of variation of said photon-equivalent dose (under the RBE model concerned) to the TV, a minimum, maximum, average, median, variance, standard deviation or coefficient of variation of said photon-equivalent dose (under the RBE model concerned) to an OAR, indicators of fulfilment of the plan goal.

In further embodiments, there may be multiple reporting quantities for each plan goal.

As used herein, a "data structure" may relate to a format for organizing data. The format may allow efficient access and modification to the data. The data structure may affect the collection of data values, the relationships among them, and the functions or operations that can be applied to the data. The data structure according to the third aspect may be stored or distributed on a data carrier.

BRIEF DESCRIPTION OF THE DRAWINGS

Aspects and embodiments are now described, by way of example, with reference to the accompanying drawings, on which:

FIG. 1 is a flowchart of a method according to an embodiment of the invention;

FIG. 2 schematically illustrates a treatment planning system according to an embodiment of the invention;

FIG. 3 is a simplified perspective view of a radiation delivery system;

FIG. 4 illustrates a data structure comprising instructions for carrying out a treatment plan as well as reporting quantities relating to a first and second plan goals corresponding to different RBE factors;

DETAILED DESCRIPTION

Figure 5:
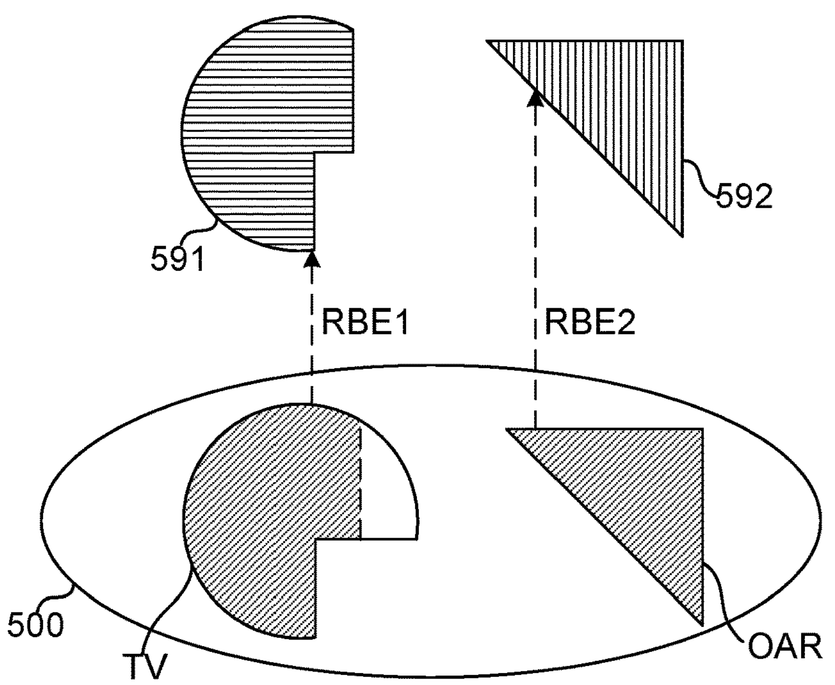
FIG. 5 contains, in a lower portion, a schematic section view of a radiotherapy patient where a TV and an OAR are identified, and, in an upper portion, two volumes within the TV and OAR, respectively, to which plan goals apply.

The aspects of the present disclosure will now be described more fully with reference to the accompanying drawings, on which certain embodiments of the invention are shown. These invention may, however, be embodied in many different forms and the embodiments should not be construed as limiting; rather, they are provided by way of example so that this disclosure will be thorough and complete, and to fully convey the scope of all aspects of invention to those skilled in the art.

FIG. 1 is a flowchart of an inverse-planning method 100 for generating a treatment plan specifying a non-photon irradiation of a patient 500 (FIG. 5), 600 (FIG. 6) including a target volume TV.

The method 100 may be implemented in a treatment planning system 200 of the type illustrated in FIG. 2. The treatment planning system may include an interface 210, a memory 220 and processing circuitry 230. The interface 210 is configured to receive at least a first and a second plan goal, such as by operator input via a graphical user interface or by data transfer. The interface 210 may connect the treatment planning system 200 to a data network, so as to enable communication with users, clinicians, researchers, treatment planning personnel, radiation delivery systems etc. The memory 220 may be configured to store a computer program 221 with instructions for causing the treatment planning system 200 to carry out the method 100. The processing circuitry 230 may execute the instructions of the computer program 221, in particular to carry out an optimization process.

In a first step 110, a first plan goal in terms of a first numerical condition on the treatment plan's photon-equivalent dose as computed using a first RBE factor is obtained. The first plan goal may be obtained by being input by an operator, received by transfer of a data file from a portable memory, over a network or through an email service. Alternatively, an automated process may generate the first plan goal on the basis of patient data.

In a second step 120, the second plan goal in terms of a second numerical condition on the treatment plan's photon-equivalent dose as computed using a second, different RBE factor is obtained in one of the ways outlined for the first plan goal.

For instance, the RBE factors may be in accordance with one or more phenomenologically based parameterization of a linear energy transfer (LET) model, such as:

a Carabe model (see for example Carabe-Fernandez et al., "The incorporation of the concept of minimum RBE (RBEmin) into the linear-quadratic model and the potential for improved radiobiological analysis of high-LET treatments", *Int. J. Radiat. Biol.* (2007), vol. 83, pp. 27-39 [doi: 10.1080/09553000601087176]),

- a Chen & Ahmad model (see for example Chen et al., "Empirical model estimation of relative biological effectiveness for proton beam therapy", *Radiat. Prot. Dosim.* (2012), vol. 149, pp. 116-123 [doi: 10.1093/rpd/ncr218]),
- a McNamara model (see for example McNamara et al., "A phenomenological relative biological effectiveness (RBE) model for proton therapy based on all published in vitro cell survival data", Phys. Med. Biol. (2015), vol. 60, pp. 8399-8416 [doi: 10.1088/0031-9155/60/21/8399]),
- a Wedenberg model (see for example Wedenberg et al., "A model for the relative biological effectiveness of protons: The tissue specific parameter a/β of photons is a predictor for the sensitivity to LET changes", Acta Oncologica (2013), vol. 52, pp. 580-588 [doi: 10.3109/0284186X.2012.705892]).

The RBE factors may further be in accordance with any of:

- a local effect model (LEM) (see for example the early version described in Scholz et al., "Computation of cell survival in heavy ion beams for therapy. The model and its approximation", Radiat. Environ. Biophys. (1997), vol. 36, pp. 59-66 [doi: 10.1007/s004110050055]),
- a microdosimetric kinetic model (MKM) (see for example Hawkins, "A microdosimetric-kinetic model for the effect of non-Poisson distribution of lethal lesions on the variation of RBE with LET", *Radiat. Res.* (2003), vol. 160, pp. 61-69 [doi: 10.1667/RR3010]).

As used herein, an RBE model of a particular "type" includes not only the cited disclosure by the named author but also further developments by same or other authors, as well as quantitative and qualitative variations of the disclosed model.

A still further option is to use external software which computes the RBE factor, or equivalently, the photon-equivalent dose, on the basis of the physical dose, location particle energy and/or any further relevant factors. The software may be provided as source code which is imported into the optimization problem. Alternatively, repeated calls are made during the optimization process to a local software library. Further alternatively, and primarily if low latency can be ensured, calls are made to a web application programming interface (API). The software is external in the sense of being opaque to the treatment planner, i.e., it returns an output (photon-equivalent dose) for every admissible input (physical dose) but the treatment planner need not be aware of the RBE model that it implements or other considerations underlying the software.

The first and second plan goals satisfy option a, option b or both, as explained above.

To illustrate, FIG. 5 shows a section of a patient's body 500, where volumes TV and OAR have been identified. TV and OAR are shown completely separate (or disjoint) although it is not uncommon for these volumes to overlap to some extent, i.e., to be partially separate. A first plan goal is formulated for a subset 591 of TV using a first RBE factor RBE1; for example, it may be required that the photon-equivalent dose according to a modified Carabe model shall be at least $c_1$ units. The second plan goal applies in the volume 592, which coincides with the OAR. As an example, the second plan goal limits the delivery of photon-equivalent dose according to Chen & Ahmad at $c_2$ units. Because both RBE factors are variable, option b is satisfied.

Figure 6:
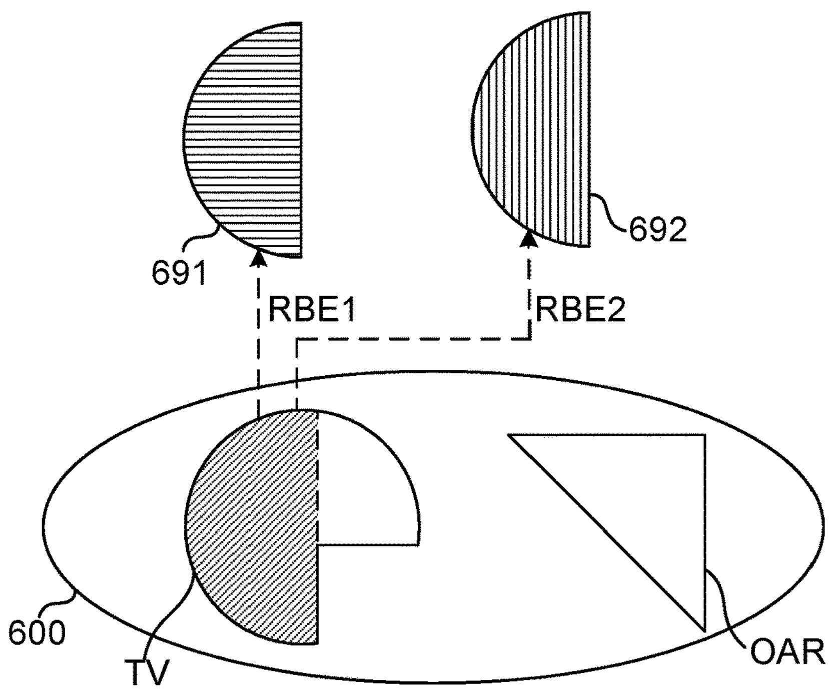
FIG. 6 is similarly structured as FIG. 5, with the difference that both plan goals apply to the same volume, which is exemplified as a subset of the TV.

Turning to FIG. 6, the first and second plan goals both relate to subsets 691, 692 of the TV. In an example case of proton irradiation, the first plan goal may be a lower bound $c_3$ on the photon-equivalent dose under the 1.1 model, and the second plan goal may be an interval $[c_4, c_5]$ for the photon-equivalent dose according to McNamara. Accordingly, option a is satisfied. Option a would have been satisfied too if the subsets 691, 692 had been volumes completely or partially separate from the TV, e.g., volumes included in the OAR.

Each plan goal is expressed as an optimization function, i.e., a component $f_i(x)$ of an objective function or a constraint $g_j(x)$, $h_k(x)$, as explained above. The objective function to be optimized is dependent on properties of the treatment plan, represented by the variable x. The treatment plan may be a description of the radiation to be delivered to the patient by a radiation source, which is positioned at a point in space with a specified orientation that may be dynamically altered during the delivery and delivers non-photon particles of a specified type and energy; the treatment plan may be expressed in terms of fluence, that is, irradiated energy per unit area of an imaginary reference surface inside or outside the patient; as a further option, the treatment plan may be expressed as instructions to a multi-leaf collimator or other beam-limiting device, or instructions for controlling a pencil beam scanning system.

The treatment plan may be intended for execution by a conventional radiation delivery system 300 as illustrated in FIG. 3. As those skilled in the art will appreciate, the radiation delivery system 300 may include a gantry with a radiation source, and a couch which a patient rests on and is fixated to during the treatment. Rotatory and/or translational relative movement between the gantry and couch is possible. In particular, the gantry may be rotatable with respect to one or two axes; and the couch may be rotatable round a vertical axis and translatable in at least one dimension. This allows a multitude of irradiation angles and positions (or incidence directions), as may be described by a corresponding plurality of fluence elements; the treatment plan may specify fluence and/or particle energy values for all or some of the available fluence elements.

It may not be explicit from a particular treatment plan how large physical dose will be absorbed in a particular volume of the patient when the treatment plan is carried out. Relatively complex computations may be required to determine or estimate the physical dose. In inverse treatment planning, the objective function may quantify the physical dose. A further layer of complexity is added if, as the invention aims to enable, the photon-equivalent dose from non-photon radiation is to be studied, especially when two different RBE factors are utilized. As one example, the objective function may be an expression that estimates the absorbed physical dose in a volume, e.g. by summing contributions from all fluence elements, then prepares an RBE factor on the basis of the physical dose, the location of the volume or other relevant factors, and finally computes the photon-equivalent dose in that volume by multiplying the RBE factor and the absorbed physical dose.

The treatment planner may have a certain latitude whether to include the plan goals into the objective function or as constraints. More precisely, there exist techniques for converting a constraint into a term in the objective function; such term may be a barrier function or indicator function assigning a penalty to x values violating the constraint. There are also ways to translate a component of the objective function into one or more constraints, including linearization techniques and preconditioning techniques. In different embodiments of the invention, the first and second goals may be included as optimization functions being two objective function components, two constraints or a one optimization function of each type.

The optimization problem P may have the following appearance:

$$\min_{x \in A} f(x)$$

$$\text{subject to } g_j(x) \leq 0,\ j \in J$$

$$h_k(x) = 0,\ k \in K$$

where A represents the set of admissible treatment plans, where one or both of the constraint index sets J, K may be empty, and where the first and second plan goals have been included in the objective function or the constraints.

In a third step 114, the treatment plan is generated by means of an optimization process aiming to satisfy the first, second and any further plan goals by solving the problem P. The problem P can be solved using for example sequential quadratic programming, interior point methods, Newton's method, quasi-Newton methods, gradient descent methods, coordinate descent methods, simulated annealing, genetic algorithms, tabu search methods, or any other solver method known per se in the art.

The output of the optimization process may correspond to an optimum of the objective function or an approximate optimum striking a balance between usage of processing resources/time and acceptable accuracy of the optimum. Similarly, it may have to be accepted in the circumstances that the constraints are just approximately satisfied. The output of the optimization process may have the form of the optimizing argument x* to the objective function. The treatment plan can normally be derived in a straightforward manner from the optimizing argument x* and be put on a suitable, preferably machine-readable format to be supplied to the radiation delivery system 300. Furthermore, it may be interesting to additionally recuperate the optimal value of the objective function $f(x^*)$ or a component thereof, or an expression occurring in a constraint evaluated for the optimizing argument, $g_j(x^*)$, $h_k(x^*)$; to the extent these quantities represent the photon-equivalent dose, they are indicative of the fulfilment of the plan goals and may be used for monitoring or documentation purposes by the entity having specified the plan goals.

FIG. 4 illustrates a data structure 400 having a treatment plan component 410 comprising instructions for carrying out a treatment plan as well as a reporting component 420 reporting quantities relating to a first and second plan goals corresponding to different RBE factors. The components 410, 420 may be included as fields in a record-type data structure. The data structure 400 is well suited for storing or sharing a treatment plan together with the reporting quantities that allow inspection of the treatment plan's photon-equivalent dose under different RBE models, or of other figures of merit. The data structure 400 may be output by the interface 210 of the treatment planning system 200, eventually to be made available to the radiation delivery system 300. The data structure 400 may also be stored in the memory 220.

At least the following use cases are envisioned for the first, second and third aspects of the present invention.

Robust optimization: The invention can be used in combination with robust treatment planning, in which the effects of uncertainties (for example particle range uncertainty, setup uncertainty, organ motion, dose calculation uncertainty) are quantified and taken into account in the optimization. For example, the quanti-fication of uncertainties can be performed by the calculation of at least one dose or approximate dose resulting in at least one error scenario and the subsequent evaluation of at least one optimization function on the at least one dose. The optimization can take the error scenario dose into account in any known way of handling uncertainties, for example using techniques from robust optimization or stochastic programming or approximations thereof.

4D/multiple image set optimization: The invention can be used in combination with four-dimensional (4D) or multiple image set optimization, in which at least one image other than the planning image is taken into account in the optimization. The images can be obtained from any source, for example 4D computed tomography (4DCT), cone-beam computed tomography (CBCT), images generated using a model for generating images etc. The optimization is then performed taking the multiple images into account, for example by including optimization functions evaluated on the dose calculated for each image, or by optimization functions evaluated on the accumulated dose resulting when at least one dose is deformed and added to another image.

Multi-Criteria Optimization: The invention can be used in combination with multi-criteria optimization (MCO), in which the system generates a number of plans corresponding to different weighting of the different objective constituents, which the user then can explore to find a suitable tradeoff between the competing goals. Optimization functions using different RBE models can be included as constraints in the MCO problem, as objective constituents for which various weightings will be considered, or as objective constituents with fixed weight in all generated plans.

Lexicographic optimization: The invention can also be used in combination with lexicographic optimization techniques, in which a number of optimizations are performed sequentially. The optimization functions are included in the objective one or a few at a time, and the achieved function values (possibly with some slack) are included as constraints for the optimization functions in subsequent optimizations.

Simultaneous use of optimization objective functions based on both a constant RBE factor (e.g., 1.1) and some variable RBE model for the target. In this way the treatment planner can create a treatment plan where some small underdosage of the constant-RBE dose is allowed as long as it is made up for by the variable-RBE dose in the same volume. Further, a plan with a more uniform variable-RBE dose in the target can be generated while at the same time making sure that the constant-RBE (e.g., 1.1) dose is fulfilled.

Use of optimization objective functions based on the 1.1 model for some organs at risk and use of the variable RBE model for others. The variable RBE may be too strict for some cases, and the treatment planner may want to use his experience with the 1.1 model for them, while at the same time using the variable RBE model for others.

Simultaneous use of optimization objective functions based on the 1.1 model and some variable RBE model for an organ at risk. This may allow finding a compromise between the two, or ensuring that both are fulfilled.

Use of two or more variable RBE models for the same region of interest. This could be useful when there are uncertainties regarding which variable RBE model should be used and/or regarding different sets of parameters for the same model. This allows finding a weighted compromise between the different models, or making sure that all are fulfilled.

The aspects of the present invention have mainly been described above with reference to a few embodiments. However, as is readily appreciated by a person skilled in the art, other embodiments than the ones disclosed above are equally possible within the scope of the invention, as defined by the appended patent claims.

The invention claimed is:

1. An inverse-planning method for generating a treatment plan specifying a non-photon irradiation of a patient including a target volume, (TV), the method implemented in a treatment planning system and comprising:

obtaining a first plan goal in terms of a first numerical condition on the treatment plan's photon-equivalent dose as defined by a first relative biological effectiveness, (RBE), factor in accordance with a first RBE model;

obtaining a second plan goal in terms of a second numerical condition on the treatment plan's photon-equivalent dose as defined by a second, different RBE factor in accordance with a second RBE model, the first and second RBE models defining different photon-equivalent dose relationships; and generating the treatment plan by a single optimization process concurrently aiming to satisfy the first, second and any further plan goals, wherein at least one of the following options holds:

a) the first and second plan goals apply to volumes which either are included in the TV or are completely or partially separate from the TV, wherein either the volumes coincide or one is a subset of the other;

b) the first and second RBE factors are variable, and wherein the treatment plan is used to deliver therapeutic radiation to a patient.

2. The method of claim 1, wherein the plan goals are provided to the optimization process as optimization functions, each optimization function being either of an objective-function type or a constraint type.

3. The method of claim 2, wherein option (a) holds and both the first and second goals are provided as optimization functions of the same type.

4. The method of claim 2, wherein the first and second goals are provided as evenly or unevenly weighted terms in a common objective function.

5. The method of claim 1, wherein each variable RBE factor varies spatially and/or with respect to particle energy and/or with respect to a magnitude of the non-photon dose.

6. The method of claim 5, each variable RBE factor is in accordance with one or more of:

a Carabe-type model a Chen & Ahmad-type model, a McNamara-type model, a Wedenberg-type model, a linear energy transfer (LET) model, a local effect model (LEM), a microdosimetric kinetic model (MKM).

7. The method of claim 1, wherein each plan goal applies to a specified volume.

8. The method of claim 1, wherein the first and second plan goals correspond to different biological endpoints.

9. The method of claim 1, wherein each numerical condition includes a setpoint value, a lower bound, an upper bound or an interval.

10. The method of claim 1, wherein the non-photon irradiation includes proton irradiation.

11. A treatment planning system comprising:

an interface configured to receive at least a first and a second plan goal;

a memory; and processing circuitry configured to carry out the method of claim 1.

12. A computer program product comprising a non-transitory computer readable storage medium having program instructions embodied therewith which, when executed by a computer, cause the computer to carry out the method of claim 1.

13. A computer program product comprising a non-transitory computer readable storage medium having a data structure stored thereon, the data structure comprising:

a treatment plan component representing instructions which, when executed by a radiation delivery system, cause the system to carry out a treatment plan specifying a non-photon irradiation of a patient including a target volume, (TV); and a reporting component comprising reporting quantities relating to each of:

a first plan goal in terms of a first numerical condition on the treatment plan's photon-equivalent dose as defined by a first relative biological effectiveness, (RBE), factor in accordance with a first RBE model, and a second plan goal in terms of a second numerical condition on the treatment plan's photon-equivalent dose as defined by a second, different RBE factor in accordance with a second RBE model, the first and second RBE models defining different photon-equivalent dose relationships, wherein at least one of the following options holds:

the first and second plan goals apply to volumes which either are included in the TV or are completely or partially separate from the TV, wherein either the volumes coincide or one is a subset of the other;

the first and second RBE factors are variable, and wherein the treatment plan is used to deliver therapeutic radiation to a patient.

14. The computer program product of claim 13, wherein the reporting quantities include one or more of:

a distribution of said photon-equivalent dose for a plurality of spatial points or voxels, a dose-volume histogram for said photon-equivalent dose, a minimum, maximum, average, median, variance or standard deviation of said photon-equivalent dose to the TV, a minimum, maximum, average, median, variance or standard deviation of said photon-equivalent dose to an organ-at-risk, indicators of fulfilment of the respective plan goals.

* * * * *